(12) United States Patent
Armoundas et al.

(10) Patent No.: US 6,370,412 B1
(45) Date of Patent: Apr. 9, 2002

(54) METHOD AND APPARATUS FOR GUIDING ABLATIVE THERAPY OF ABNORMAL BIOLOGICAL ELECTRICAL EXCITATION

(75) Inventors: Antonis A. Armoundas, Cambridge, MA (US); Andrew B. Feldman, Newport, RI (US); Derin A. Sherman, Lincoln; Richard J. Cohen, Chestnut Hill, both of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/535,882

(22) Filed: Mar. 28, 2000

Related U.S. Application Data

(63) Continuation-in-part of application No. 09/413,969, filed on Oct. 7, 1999, now Pat. No. 6,308,093.

(51) Int. Cl.[7] ................................................ A61B 5/04
(52) U.S. Cl. ...................................... 600/373; 600/515
(58) Field of Search ................................ 600/509, 515, 600/518, 544, 101, 373

(56) References Cited

U.S. PATENT DOCUMENTS

| | | | |
|---|---|---|---|
| 4,522,212 A | 6/1985 | Gelinas et al. ............... | 128/642 |
| RE32,204 E | 7/1986 | Halvorsen ................... | 128/642 |
| 4,974,598 A | 12/1990 | John ........................ | 128/696 |
| 5,025,786 A | 6/1991 | Siegel ....................... | 128/642 |
| 5,056,517 A | 10/1991 | Fonici ....................... | 128/419 |
| 5,156,151 A | 10/1992 | Imran ........................ | 128/642 |
| 5,172,699 A | 12/1992 | Svenson et al. ............. | 128/705 |

(List continued on next page.)

OTHER PUBLICATIONS

Gepstein, et al., "Activation–Repolarization Coupling in the Normal Swine Endocardium", *Circulation*, 96:4036–43, 1997.

Gornick, et al., "Validation of a New Noncontact Catheter System for Electroanatomic Mapping of Left Ventricular Endocardium", *Circulation*, 99: 829–835, (1999).

Kottkamp, et al., "Three–Dimensional Electromagnetic Catheter Technology: Electroanatomical Mapping of the Right Atrium and Ablation of Ectopic Atrial Tachycardia", *J Cardiovasc Electrophysiol*, 8: 1332–37, 1997.

Mirvis, et al., "Body Surface Distributions of Repolarization Potentials after Acute Myocardial Infarction. III. Dipole Ranging in Normal Subjects and in Patients with Acute Myocardial Infarction", *J. Electrocardiology* 14(4): 387–98, 1981.

(List continued on next page.)

*Primary Examiner*—Scott M. Getzow
(74) *Attorney, Agent, or Firm*—Choate, Hall & Stewart; Monica R. Gerber

(57) ABSTRACT

This invention involves method and apparatus for guiding ablative therapy of abnormal biological electrical excitation. In particular, it is designed for treatment of cardiac arrhythmias. In the method of this invention electrical signals are acquired from passive electrodes, and an inverse dipole method is used to identify the site of origin of an arrhythmia. The location of the tip of the ablation catheter is similarly localized from signals acquired from the passive electrodes while electrical energy is delivered to the tip of the catheter. The catheter tip is then guided to the site of origin of the arrhythmia, and ablative radio frequency energy is delivered to its tip to ablate the site.

44 Claims, 4 Drawing Sheets

U.S. PATENT DOCUMENTS

| | | | |
|---|---|---|---|
| 5,237,996 A | 8/1993 | Waldman et al. | 128/642 |
| 5,255,679 A | 10/1993 | Imran | 128/642 |
| 5,282,845 A | 2/1994 | Bush et al. | 607/128 |
| 5,297,549 A | 3/1994 | Beatty et al. | 128/642 |
| 5,311,866 A | 5/1994 | Kagan et al. | 128/642 |
| 5,311,873 A | 5/1994 | Savard et al. | 128/696 |
| 5,324,284 A | 6/1994 | Imran | 606/15 |
| 5,327,889 A | 7/1994 | Imran | 128/642 |
| 5,385,146 A | 1/1995 | Goldreyer | 128/642 |
| 5,391,199 A | 2/1995 | Ben-Haim | 607/122 |
| 5,406,946 A | 4/1995 | Imran | 128/642 |
| 5,429,131 A | 7/1995 | Scheinman et al. | 128/642 |
| 5,443,489 A | 8/1995 | Ben-Haim | 607/115 |
| 5,450,846 A | 9/1995 | Goldreyer | 128/642 |
| 5,480,422 A | 1/1996 | Ben-Haim | 607/122 |
| 5,507,802 A | 4/1996 | Imran | 607/128 |
| 5,546,951 A | 8/1996 | Ben-Haim | 128/702 |
| 5,551,426 A | 9/1996 | Hummel et al. | 128/642 |
| 5,553,611 A | 9/1996 | Budd et al. | 128/642 |
| 5,657,755 A | 8/1997 | Desai | 128/642 |
| 5,662,108 A | 9/1997 | Budd et al. | 128/642 |
| 5,680,860 A | 10/1997 | Imran | 128/642 |
| 5,782,889 A | 7/1998 | Imran | 607/122 |
| 5,788,692 A | 8/1998 | Campbell et al. | 606/33 |
| 5,840,025 A | 11/1998 | Ben-Haim | 600/424 |
| 5,846,198 A | 12/1998 | Killmann | 600/424 |
| 5,848,972 A | 12/1998 | Triedman et al. | 600/508 |

OTHER PUBLICATIONS

Nademanee, et al., "A Nonfluoroscopic Catheter–Based Mapping Technique to Ablate Focal Ventricular Tachycardia" PACE, 21: 1442–47, (1998).

Nakagawa, et al., "Use of a Three–Dimensional, Nonfluoroscopic Mapping System for Catheter Ablation of Typical Atrial Flutter", PACE, 21: 1279–86, (1998).

Natale, et al., "Ablation of Right and Left Ectopic Atrial Tachycardias Using a Three–Dimensional Nonfluorescopic Mapping System", *The American Journal of Cardiology* , 82:989–92, (1998).

Paul, et al., "Epicardial Mapping: How to Measure Local Activation?", PACE, 13: 285–92, 1990.

Schilling, et al., "Characteristics of Sinus Rhythm Electrograms at Sites of Ablation of Ventricular Tachycardia Relative to All Other Sites: A Noncontact Mapping Study of the Entire Left Ventricle", *J Cardiovasc Electrophysiol*, 9: 921–33, (1998).

Shah, et al., "Three–Dimensional Mapping of the Common Atrial Flutter Circuit in the Right Atrium" *Circulation* 96(11): 3904–12, (1997).

Shpun, et al., "Guidance of Radiofrequency Endocardial Ablation with Real–Time Three–Dimensional Magnetic Navigation System" *Circulation*, 96(6): 2016–21, (1997).

Smith, et al., "Electrical Alternans and Cardiac Electrical Instability", *Circulation*, 77(1): 110–21, (1988).

Stevenson, et al., "Identification and Ablation of Macroreentrant Ventricular Tachycardia with the CARTO Electroanatomical Mapping System", *PACE*, 21: 1448–56, (1998).

Stevenson, et al., "Radiofrequency Catheter Ablation of Ventricular Tachycardia Late After Myocardial Infarction", *Journal of Cardiovascular Electrophysiology* 8(11): 1309–19,.

Stevenson, et al., "Radiofrequency Catheter Ablation of Ventricular Tachycardia After Myocardial Infarction", *Circulation*, 98: 308–14, 1998.

Strickberger, et al., "A Prospective Evaluation of Catheter Ablation of Ventricular Tachycardia as Adjuvant Therapy in Patients with Coronary Artery Disease and an Implantable Cardioverter–Defibrillator", *Circulation*, 96:1525–31, 1997.

METHOD AND APPARATUS FOR GUIDING ABLATIVE THERAPY OF ABNORMAL BIOLOGICAL ELECTRICAL EXCITATION

CROSS REFERENCE TO RELATED APPLICATION

This application is a continuation in part of U.S. application Ser. No. 09/413,969 filed Oct. 7, 1999 now U.S. Pat. No. 6,308,093. +gi

GOVERNMENT SUPPORT

The U.S. Government has a paid-up license in this invention and the right in limited circumstances to require the patent owner to license others on reasonable terms as provided for by the terms of Grant No. NAG5-4989 awarded by the National Aeronautics and Space Administration.

BACKGROUND OF THE INVENTION

The electrical activity generated in certain organs in the human body is intimately related to their function. Abnormalities in cardiac and brain electrical conduction processes are principal causes of morbidity and mortality in the developed world. Appropriate treatment of disorders arising from such abnormalities frequently requires a determination of their location. Such localization of the site of origin of an abnormal electrical excitation is typically achieved by painstaking mapping of the electrical activity on the inner surface of the heart or the brain from electrodes or a catheter. Often, this recording must be done while the abnormal biological electrical excitation is ongoing.

Radio frequency catheter ablation procedures have evolved in recent years to become an established treatment for patients with a variety of supraventricular [Lee, 1991; Langberg, 1993] and ventricular arrhythmias [Stevenson, 1997; Stevenson, 1998]. However, in contrast to supraventricular tachycardia ablation, which is highly successful because the atrio-ventricular node anatomy is known, ventricular tachycardia ablation remains difficult because the site of origin of the arrhythmia could be anywhere in the ventricles.

Sustained ventricular tachycardia is often a difficult arrhythmia to manage. One of the most common indications for radio frequency catheter ablation of ventricular tachycardia is arrhythmia refractory to drug therapy that results in frequent discharges from an implantable cardioverter-defibrillator. Radio frequency ablation is also indicated when the ventricular tachycardia (VT) is too slow to be detected by the implantable cardioverter-defibrillator or is incessant [Strickberger, 1997].

Selection of the appropriate target sites for ablation is usually based on a combination of anatomical and electrical criteria. The ability of the physician to deliver radio frequency energy through a catheter at the reentry site is restricted by the limitations of the current technology that is employed to guide the catheter to the appropriate ablation site. The principal limitation of the radio frequency ablation technique is the determination of the correct site for delivery of the radio frequency energy. Conventionally, this determination is achieved by painstaking mapping of the electrical activity on the inner surface of the heart from electrodes on the catheter. Often, this recording must be done while the arrhythmia is ongoing. This is a major problem, especially for those arrhythmias which compromise hemodynamic function of the patient. Many arrhythmias for this reason are not presently amenable to radio frequency ablation treatment.

The acute lesion created by radio frequency current consists of a central zone of coagulation necrosis surrounded by a zone of hemorrhage and inflammation. Arrhythmias may recur if the target tissue is in the border zone of a lesion instead of in the central area of necrosis. If the inflammation resolves without residual necrosis, arrhythmias may recur several days to several weeks after an apparently successful ablation [Langberg, 1992]. Conversely, an arrhythmia site of origin that was not initially successfully ablated may later become permanently nonfunctional if it lies within the border zone of a lesion and if microvascular injury and inflammation within this zone result in progressive necrosis [Nath, 1994]. Thus, the efficacy and long term outcome of catheter ablation depend on accurate determination of the site of origin of the arrhythmia.

Catheter ablation of sustained monomorphic ventricular tachycardia late after myocardial infarction has been challenging. These arrhythmias arise from reentry circuits that can be large and complex, with broad paths and narrow isthmuses, and that may traverse subendocardial, intramural, and epicardial regions of the myocardium [deBakker, 1991; Kaltenbrunner, 1991].

Mapping and ablation are further complicated by the frequent presence of multiple reentry circuits, giving rise to several morphologically different VTs [Wilbur, 1987; Waspel, 1985]. In some cases, different reentry circuits form in the same abnormal region. In other cases, reentry circuits form at disparate sites in the infarct area. The presence of multiple morphologies of inducible or spontaneous VT has been associated with antiarrhythmic drug inefficacy [Mitrani, 1993] and failure of surgical ablation [Miller, 1984].

Several investigators have reported series of studies of patients selected for having one predominant morphology of VT ("clinical VT") who were treated with radio frequency catheter ablation [Morady, 1993; Kim, 1994]. It is likely that this group of patients represents less than 10% of the total population of patients with VT [Kim, 1994]. The patient must remain hemodynamically stable while the arrhythmia is induced and maintained during mapping. The mapping procedure may take many hours during which the arrhythmia must be maintained. Thus, currently radio frequency catheter ablation is generally limited to "slow" ventricular tachycardia (~130 bpm) which is most likely to be hemodynamically stable.

Ablation directed towards the "clinical tachycardia" that did not target other inducible VTs successfully abolished the "clinical VT" in 71% to 76% cases. However, during followup up to 31% of those patients with successful ablation of the "clinical VT" had arrhythmic recurrences, some of which were due to different VT morphologies from that initially targeted for ablation.

Furthermore, there are several difficulties in selecting a dominant, "clinical VT" for ablation. Often it is not possible to determine which VT is in fact the one that has occurred spontaneously. In most cases, only a limited recording of one or a few ECG leads may be available. In patients with implantable defibrillators VT is typically terminated by the device before an ECG is obtained. Even if one VT is identified as predominant, other VTs that are inducible may subsequently occur spontaneously. An alternative approach is not to consider the number of VT morphologies in determining eligibility for catheter ablation but rather to attempt ablation of all inducible VTs that are sufficiently tolerated to allow mapping [Stevenson, 1998b; Stevenson, 1997]. However, this approach requires that the patient be hemodynamically stable during the VT mapping procedure.

The use of fluoroscopy (digital bi-plane x-ray) for the guidance of the ablation catheter for the delivery of the curative radio frequency energy is common to clinical catheter ablation strategies. However, the use of fluoroscopy for these purposes may be problematic for the following reasons: (1) It may not be possible to accurately associate intracardiac electrograms with their precise location within the heart; (2) The endocardial surface is not visible using fluoroscopy, and the target sites can only be approximated by their relationship with nearby structures such as ribs and blood vessels as well as the position of other catheters; (3) Due to the limitations of two-dimensional fluoroscopy, navigation is frequently inexact, time consuming, and requires multiple views to estimate the three-dimensional location of the catheter; (4) It may not be possible to accurately return the catheter precisely to a previously mapped site; (5) It is desirable to minimize exposure of the patient and medical personnel to radiation; and (6) Most importantly, fluoroscopy cannot identify the site of origin of an arrhythmia and thus cannot be used to specifically direct a catheter to that site.

Electro-anatomic mapping systems (e.g., Carto, Biosense, Marlton, N.J.) provide an electro-anatomical map of the heart. This method of nonfluoroscopic catheter mapping is based on an activation sequence to track and localize the tip of the mapping catheter by magnetic localization in conjunction with electrical activity recorded by the catheter. This approach has been used in ventricular tachyardia [Nademanee, 1998; Stevenson, 1998], atrial flutter [Shah, 1997; Nakagawa, 1998], and atrial tachycardia ablation [Natale, 1998; Kottkamp, 1997]. The ability to localize in space the tip of the catheter while simultaneously measuring the electrical activity may facilitate the mapping process. However, this technique fundamentally has the limitation that it involves sequentially sampling endocardial sites. The mapping process is prolonged while the patients must be maintained in VT. Also, the localization is limited to the endocardial surface and thus sites of origin within the myocardium cannot be accurately localized.

The basket catheter technique employs a non-contact 64-electrode basket catheter (Endocardial Solutions Inc., St. Paul, Minn.) placed inside the heart to electrically map the heart. In the first part of this procedure high frequency current pulses are applied to a standard catheter used in an ablation procedure. The tip of this catheter is dragged over the endocardial surface, and a basket catheter is used to locate the tip of the ablation catheter and thus to trace and reconstruct the endocardial surface of the ventricular chamber. Then the chamber geometry, the known locations of the basket catheter, and the non-contact potential at each electrode on the basket catheter are combined in solving Laplace's equation, and electrograms on the endocardial surface are computed. This technique has been used in mapping atrial and ventricular arrhythmias [Schilling, 1998; Gornick, 1999]. One of the drawbacks of this methodology is that the ventricular geometry is not fixed but varies during the cardiac cycle. In addition, the relative movement between the constantly contracting heart and the electrodes affects the mapping. While the inter-electrode distances on each sidearm of the basket catheter are fixed, the distances between the actual recording sites on the endocardium decrease during systole. This leads to relative movement between the recording electrode and the tissue, significantly limiting the accuracy of the mapping method. Also, the localization is limited to the endocardial surface, and thus sites of origin within the myocardium cannot be accurately localized.

What is needed is a means of efficiently directing the tip of a catheter to a site of origin of an arrhythmia in the heart (whether on the endocardial surface or within the myocardium itself), without the need to introduce additional passive electrodes into the heart, so that energy can be delivered through the catheter to ablate the site of origin. It would be advantageous to be able to accomplish this task without having to maintain the arrhythmia while advancing the catheter to the site of origin, so that the patient does not suffer the ill effects of the arrhythmia for a prolonged period. This consideration is particularly important in the case of rapid arrhythmias that compromise hemodynamic function.

SUMMARY OF THE INVENTION

The present invention provides methods and apparatus for localizing an electrical source within the body. The invention further provides methods and apparatus for delivering ablative electrical energy in the vicinity of an electrical source within the body. The electrical source may be located anywhere within the body. For example, the electrical source may be within the heart and may be the site of origin of a cardiac arrhythmia. The electrical source may be a focus of electrical activity within the brain, such as a site involved in triggering an epileptic seizure, or may be located in other neurological tissue.

Cardiac arrhythmias are frequently treated by delivering electrical energy to the site of origin of the arrhythmia in an effort to ablate the site. To effectively perform this procedure, accurate localization of both the site of origin of the arrhythmia and the energy delivery device (e.g., the tip of a catheter) is necessary. As used herein, the term "localization" refers to determining either an absolute or a relative location. The present invention provides techniques for accurately performing such localization. The minimally invasive and fast aspects of certain embodiments of the invention, as disclosed herein, are particularly important.

In preferred embodiments the methods of the present invention involve placing passive electrodes on the body surface, placing active electrode(s) in and/or on the body, acquiring from the passive electrodes signals emanating from the electrical source, processing the signals emanating from the electrical source to determine the relative location of the electrical source, delivering electrical energy to the active electrode(s), acquiring from the passive electrodes the signals emanating from the active electrode(s), processing the signals emanating from the active electrode(s) to determine the relative location of the active electrode(s), and positioning the active electrode(s) to localize the electrical source. In another embodiment at least one of the passive electrodes is placed within the body, for example within the heart. The positioning step of the present invention may involve approximating the relative locations of the active electrode(s) and the electrical source. In preferred embodiments of the method the energy delivering step, the second acquiring step, the second processing step and the positioning step are performed iteratively.

In a preferred embodiment the first processing step is used to determine the relative location of the electrical source at a multiplicity of time epochs during the cardiac cycle, and the positioning step localizes the electrical source at one of the time epochs. At least one criterion may be used to choose the time epoch. In a particularly preferred embodiment at least one of the processing steps involves fitting the acquired signals to a moving dipole model. In a particularly preferred embodiment of the invention the second processing step includes determining the relative location of a moving dipole that is approximately parallel to the moving dipole fitted in the first processing step to signals emanating from the electrical source. In one embodiment, such determination is made using a multiplicity of active electrodes.

Another preferred embodiment of the invention involves delivering ablative energy in the vicinity of the location of an electrical source within the body by delivering ablative energy in the vicinity of the location of the active electrode (s). The active electrode(s) may be located on a catheter, and the ablative energy may be delivered through the catheter. In a preferred embodiment the ablative energy is radio frequency energy.

The methods of the present invention may further include displaying various parameters. Among the parameters of interest are the relative location of the electrical source and measures of the size, strength, and/or uncertainty in the relative location of the electrical source.

Other features and advantages of the invention will become apparent from the following description, including the drawing, and from the claims.

DESCRIPTION OF PREFERRED EMBODIMENTS

Figure 1:
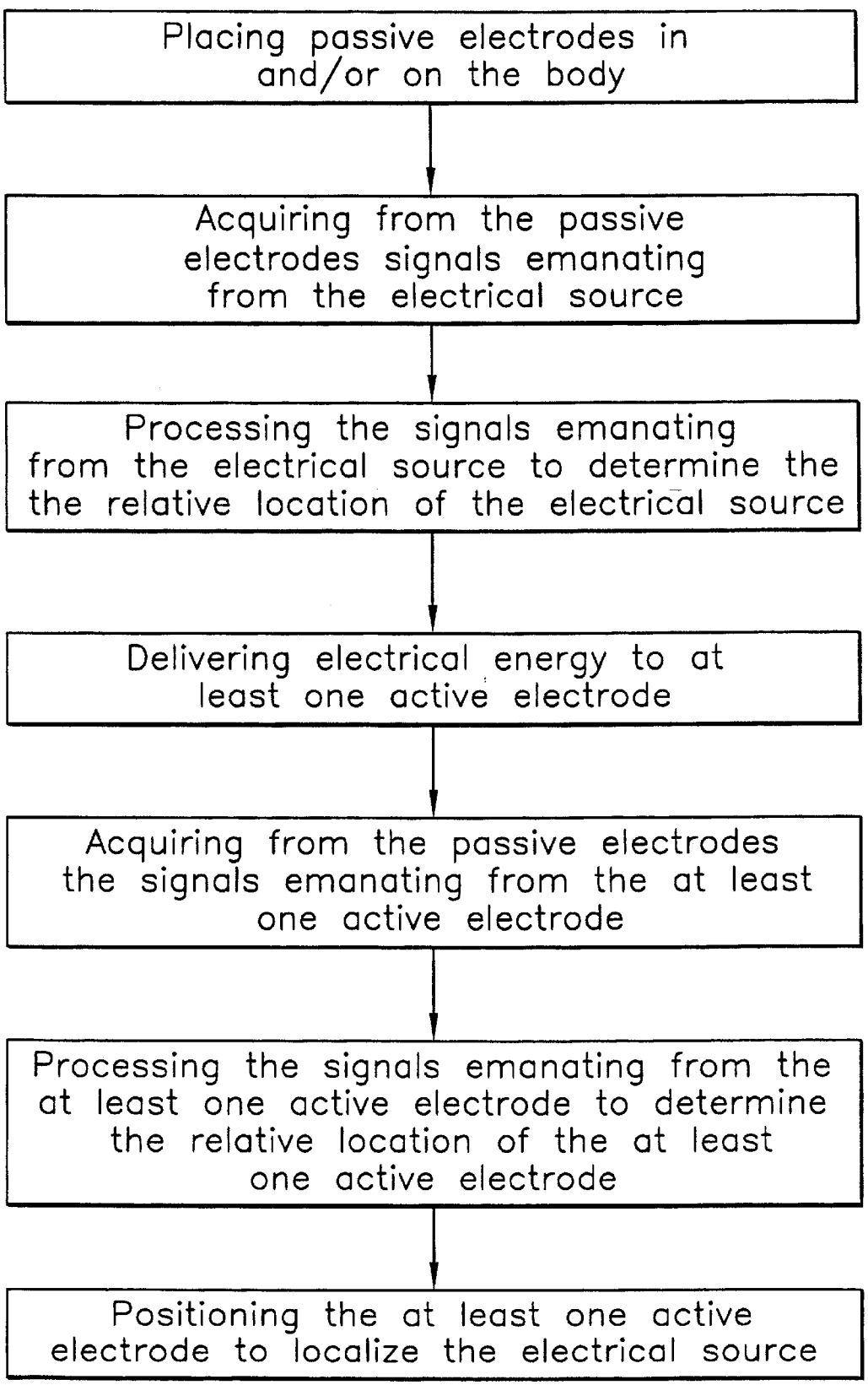
FIG. 1 is a flow chart of the method for localizing an electrical source within the body.

The present invention encompasses the finding that by employing a moving dipole model it is possible to accurately localize a source of electrical energy within the body relative to the location of an active electrode. If one can localize the site of origin of an arrhythmia during the cardiac cycle, it is possible to ablate the site through delivery of ablative electrical energy. The present invention provides methods and apparatus for localizing an electrical source within the body. The invention further provides methods and apparatus for localizing and ablating the site of origin of a cardiac arrhythmia.

The concept of considering the heart as a single dipole generator originated with Einthoven [Einthoven, 1912], and its mathematical basis was established by Gabor and Nelson [Gabor, 1954]. Several investigators [Mirvis, 1981; Gulrajani, 1984], Tsunakawa, 1987] have studied the cardiac dipole in clinical practice and attempted to determine the dipolar nature of the ECG. The advantages of the use of the equivalent cardiac dipole are: (1) It permits quantification of source strength in biophysical terms that are independent of volume conductor size (classic electrocardiography), and (2) The active equivalent source can be localized and assigned a location, something that cannot be done using classical electrocardiography.

For many arrhythmias, the electrical activity within the heart is highly localized for a portion of the cardiac cycle. During the remainder of the cardiac cycle the electrical activity may become more diffuse as the waves of electrical activity spread. It is not possible to construct the three-dimensional distribution of cardiac electrical sources from a two-dimensional distribution of ECG signals obtained on the body surface. However, if it is known that a source is localized, then this localized source can be approximated as a single equivalent moving dipole (SEMD), for which one can compute the dipole parameters (i.e., location and moments) by processing electrocardiographic signals acquired from passive electrodes placed on the body surface or in the body.

Fitting the dipole parameters to body surface ECG signals provides a solution (referred to herein as the inverse solution) for the dipole location (as well as for its strength and orientation). The location of the dipole at the time epoch when the electrical activity is confined to the vicinity of the site of origin of an arrhythmia should coincide with the site of origin of the arrhythmia. In contrast to standard mapping techniques, the inverse solution can be computed from only a few beats of the arrhythmia, thereby eliminating the need for prolonged maintenance of the arrhythmia during the localization process. In addition, if one delivers low-amplitude bipolar current pulses to the tip of an ablation catheter and acquires the resulting body surface signals, the tip of the catheter may likewise be modeled as a single equivalent moving dipole. Therefore, the same inverse algorithm may be employed to localize the tip of the catheter. Using this information one can guide the tip of the catheter to the site of origin of the arrhythmia.

The confounding factors of the SEMD method involve the fact that, as described above, the method does not consider boundary conditions and inhomogeneities in tissue conductivity. Furthermore, even the exact position of the passive acquiring electrodes in three-dimensional space may not be accurately determined. Thus the inverse solution obtained is distorted. However, as long as the site of origin of the arrhythmia and the tip of the catheter are identified using the same algorithm, then when the two are brought together, both their positions will be distorted by the same amount. In other words, when the algorithm identifies that the site of origin of the arrhythmia and the catheter tip are at the same location, then they are at the same location. Thus the distortion due to the above factors should not significantly affect the accuracy by which one can make the tip of the ablation catheter and the site of origin of the arrhythmia coincide. Therefore, although the SEMD method described herein may not establish the absolute locations of the site of origin of the arrhythmia and the tip of the catheter, it can effectively identify their relative locations.

FIG. 1 shows a flowchart of the method according to the present invention for localizing an electrical source within the body. The method includes placing passive electrodes in or on the body to acquire electrical signals. The signals from the passive electrodes are processed to determine the relative location of the electrical source within a given short time epoch. The processing steps are repeated for multiple sequential time epochs, and the location of the source corresponding to the site of the origin of the arrhythmia is obtained. As used herein, the phrase "sequential time epochs" does not necessarily imply immediately successive time epochs.

As further shown in FIG. 1, electrical energy is delivered from at least one active electrode placed within or on the body, and the signals emanating from the at least one active electrode (e.g., at the tip of a catheter) are acquired from the passive electrodes. Signals emanating from the at least one active electrode are processed to determine the relative location of the at least one active electrode within a given short time epoch. Thereafter, the processes of delivering electrical energy and determining the relative location of at least one active electrode are repeated until the active electrode is superposed to the relative location of the electrical source. In other words, in a preferred embodiment of the invention, the processes of delivering electrical energy to the at least one active electrode, acquiring from the passive electrodes the signals emanating from the at least one active electrode, processing the signals emanating from the at least one active electrode, and positioning the at least one active electrode are performed iteratively. This repetition of steps 4 through 7 of FIG. 1 may be terminated when the relative locations of the electrical source and the active electrode are within a predetermined distance (not shown on FIG. 1).

The present invention provides method and apparatus for guiding ablative therapy within an organ system either from body surface electrodes or from internal electrodes. This technique explicitly recognizes that one cannot uniquely reconstruct from a two-dimensional array of electrodes a three-dimensional distribution of sources. The present invention models bio-electrical activity as a single equivalent moving dipole (SEMD), which is a valid model when the bio-electrical activity is highly localized. In the cardiac context, the evolution of the SEMD during the cardiac cycle provides a three-dimensional picture of cardiac electrical activity.

The basic theory of the present invention derives from electromagnetic theory. The potential due to a dipole in an infinite homogeneous volume conductor is given by the equation below.

$$\phi^i = \frac{p \cdot (r^i - r')}{|r^i - r'|^3} \quad \text{(Eq. 1)}$$

where, $r^i$ is the three-dimensional vector representing the $i_{th}$ observation location, p is the three-dimensional vector representing the dipole moment, and r' is the three-dimensional vector representing the dipole location.

One may obtain the dipole parameters, i.e., p and r', from potential measurements through minimization of an objective function. One may use chi-square ($\chi^2$) as the objective function to obtain the dipole parameter estimates. $\chi^2$ is given by equation 2 below:

$$\chi^2 = \sum_{i=1}^{I} \left( \frac{\phi^i - \phi_m^i}{\sigma^i} \right)^2 \quad \text{(Eq. 2)}$$

where $\phi^i$ is the potential at the $i_{th}$ electrode because of the specific dipole components, $\phi_m^i$ is the measured potential at the $i_{th}$ electrode, $\sigma^i$ is a noise measurement at the $i_{th}$ electrode, and I is the number of electrodes.

Because of the linear dependence of the potential (Eq. 1) on the dipole moment parameters, the latter can be separated from the spatial dipole parameters. Consequently, any optimization method may be applied to the spatial parameters only, while an analytic optimization procedure may be performed to obtain the optimal fitting dipole moment parameters for a specific set of dipole spatial parameters. We coin the term 3 plus 3 parameter optimization for this algorithm.

Using the $\chi^2$ as an objective function the optimal dipole moment components ($p_x$, $p_y$, $p_z$) at each dipole location can be obtained by solving the following system of equations:

$$0 = \frac{\partial \chi^2}{\partial p_k} \quad \text{(Eq. 3)}$$

$$= \sum_{i=1}^{I} \frac{\partial \chi^2}{\partial \varphi_m^i} \frac{\partial \varphi_m^i}{\partial p_k}$$

$$= 2 \sum_{i=1}^{I} \frac{\varphi^i - \varphi_m^i}{\sigma_i^2} r_k^i - \frac{r_k'}{|r^i - r'|^3}, k = 1, 2, 3$$

and after substituting Eq. 1 into Eq. 3, we obtain $$\sum_{j=1}^{3} p_j \alpha_{kj} = \beta_k \quad \text{(Eq. 4)}$$

where $$\alpha_{kj} = \sum_{i=1}^{I} \frac{(r_k^i - r_k')(r_j^i - r_j')}{|r^i - r'|^6} \quad \text{(Eq. 5)}$$

and $$\beta_k = \sum_{i=1}^{I} \frac{\phi^i (r_k^i - r_k')}{|r^i - r'|^3} \quad \text{(Eq. 6)}$$

Thus, the potential is now given by an equation of the form $\phi^i = \phi^i(p(r'), r')$, where $p(r')$ represents the optimal dipole moment at the location r'. This equation can now be solved for all dipole moment components $p_k$.

In a preferred embodiment of the invention the moving dipole model presented above is employed to localize a source of electrical activity within the body (e.g., a site of origin of a cardiac arrhythmia) and to localize at least one active electrode (e.g., the tip of a catheter). According to the invention, passive electrodes are used to acquire ECG potentials from the body. Following data acquisition, each of the body surface ECG channels is examined to secure good data quality. Inadmissible data could occur, for example, due to (1) lack of contact of the electrodes to the skin or other body tissue, or (2) electrode failure during the procedure.

Following confirmation that the data quality is adequate, in preferred embodiments of the invention the data is preprocessed. In a preferred embodiment, the R wave in the QRS complex is identified in each ECG beat and for each channel and subsequently the baseline of each beat is adjusted relative to an identified PR segment. Baseline correction includes estimation of the baseline in the isoelectric PR segment by averaging successive samples in this time window for each lead and subsequently subtracting this estimate before construction of the vector magnitude. The resulting annotations and RR intervals may be displayed and graphically examined for evidence of spurious and/or undetected events. Then, fiducial points are determined by an adaptive QRS template matching scheme to refine initial fiducial point estimates. For this refinement phase the vector magnitude waveform of the QRS complex from standard ECG leads (I, II, III) is calculated for each beat. This is performed by calculating the square root of the sum of the squares of each of the three baseline-corrected standard leads. The average vector magnitude QRS complex is then calculated with the use of initial fiducial point estimates. With this average as a template, the fiducial points corresponding to each QRS complex are shifted to maximize the cross-correlation between each beat and the template [Smith, 1988]. Next, a median beat is created to represent each data segment by aligning each beat within the data segment according to the R wave, and identifying the median value on a time epoch-by-time epoch basis within the beat. After estimation of the median beat for each channel, a noise estimate will be obtained from each median beat (and channel) in a predefined noise window.

Figures 1, 2:
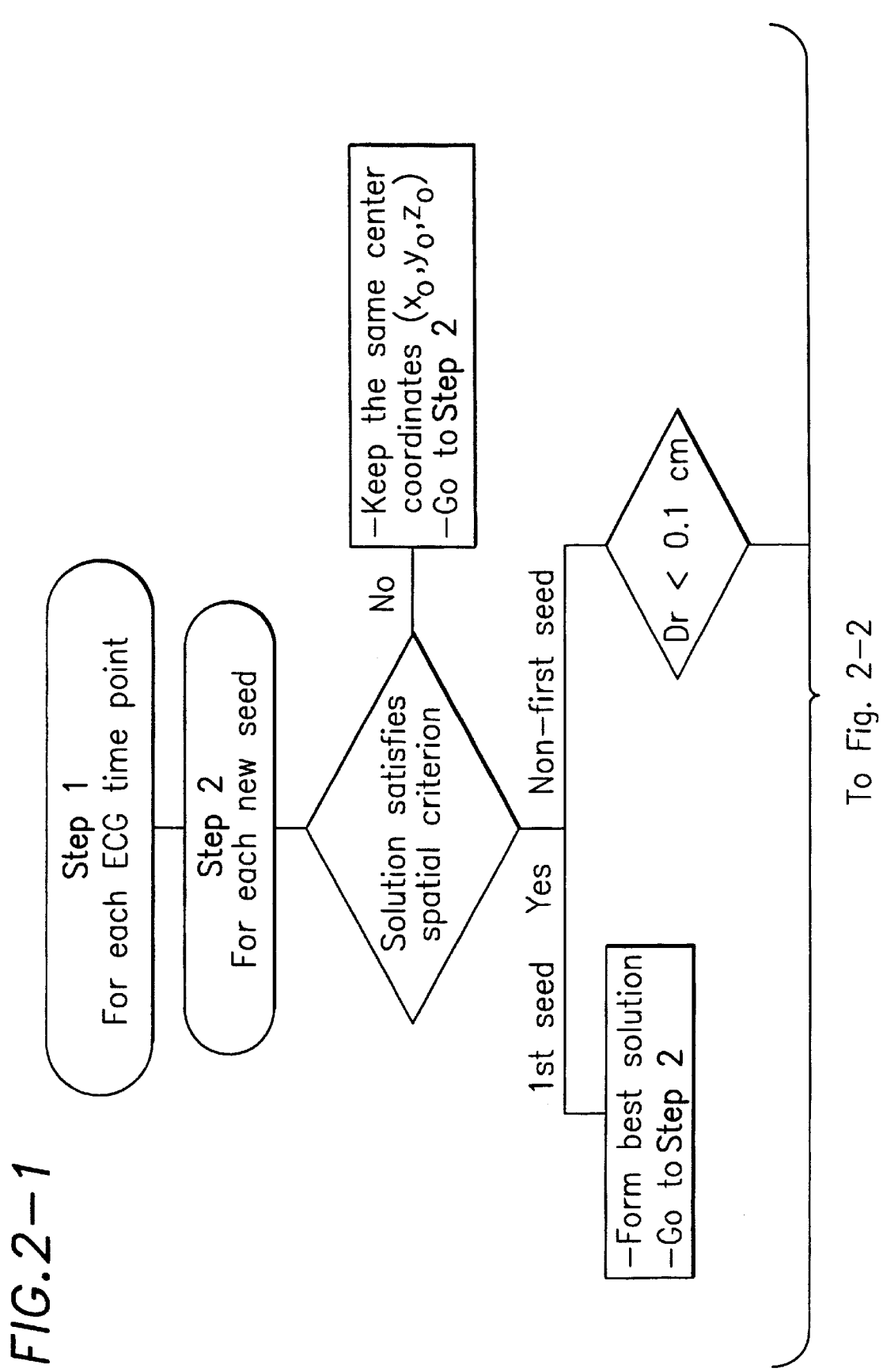
FIG. 2 is a flow chart of a procedure for fitting single equivalent moving dipole parameters to ECG potentials.
Figure 2:
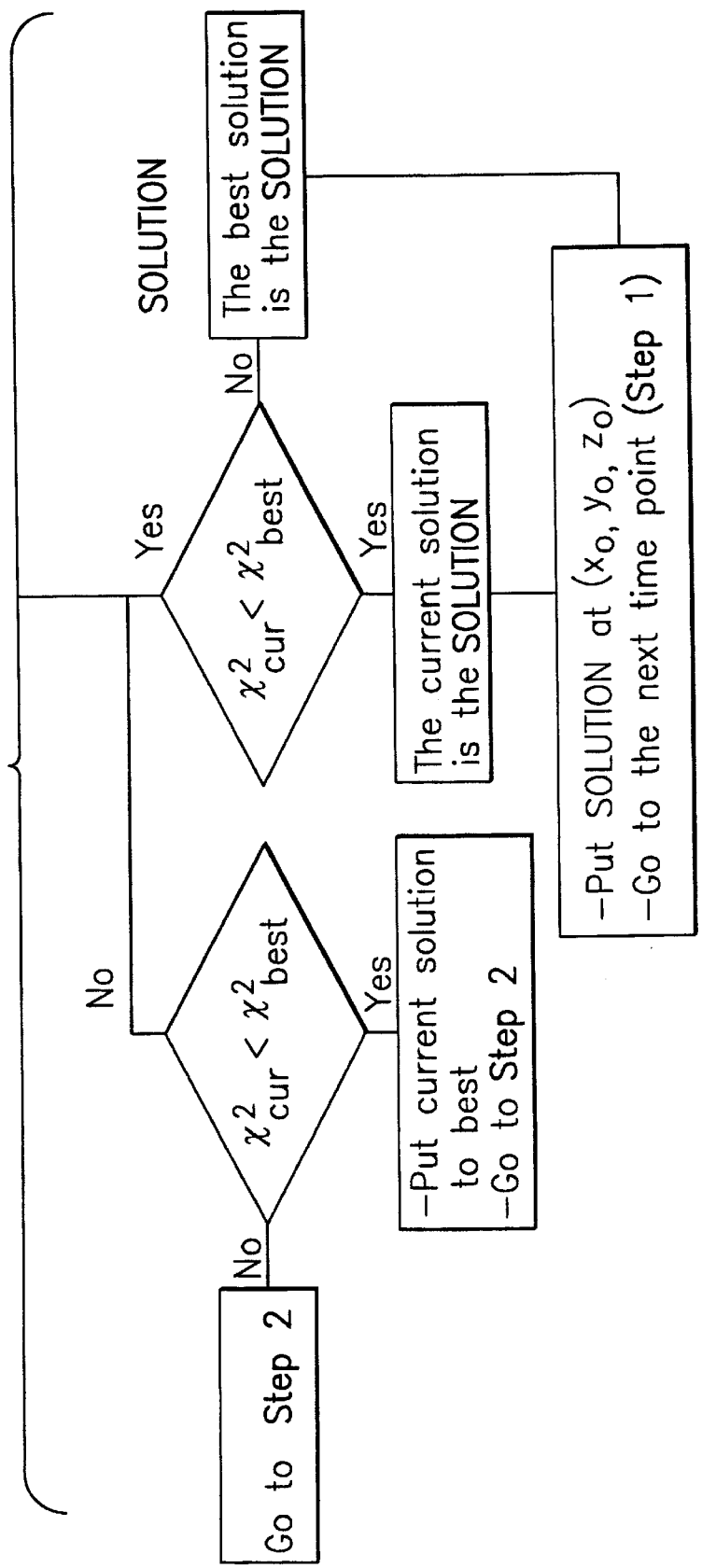

After completion of the preprocessing of the data, an algorithm to fit the single equivalent moving dipole (SEMD) parameters to the ECG potentials is applied for every time epoch in the cardiac cycle. In a preferred embodiment of the invention the algorithm shown in FIG. 2 is employed. This algorithm utilizes a multiple seed value search (e.g., a maximum of ten seeds). A spatial criterion is imposed to eliminate solutions that land outside a predefined volume (e.g., the volume of the body). The distance, $D_r$, between the location of the solution resulting from each seed (i.e., the current location) and the location of the best previous solution is determined. If the distance ($D_r$) is not less than 0.1 cm and the $\chi^2$ of the current solution ($\chi 2_{cur}$) is less than the $\chi^2$ of the best solution obtained thus far ($\chi^2_{best}$), then the current solution becomes the new best solution. Alternatively, if $D_r<0.1$ cm then the final solution is set to whichever of either the current solution or the best previous solutions has the lower $\chi^2$. The algorithm is terminated when two solutions are found to be closer than approximately 0.1 cm. Note that the two solutions need not necessarily be successive solutions. A solution obtained for a particular time epoch in a given cardiac cycle serves as the initial seed for the next time epoch. If, after all seeds are used, no solutions have been found within a given time epoch that satisfy the spatial criterion and are closer together than approximately 0.1 cm, the algorithm outcome will be considered nonconvergent for that time epoch.

In another embodiment, an algorithm able to perform beat-to-beat analysis (continuous analysis) across all channels can be employed in the processing step. This algorithm has the ability to select a baseline segment before each QRS complex for individual beat noise estimation. Since, for each time epoch, the algorithm obtains N solutions that correspond to the best solutions of the same time epoch for the N beats, the selection of the solution with the smallest error in predicting the potentials measured on the electrodes is chosen to be the best solution for that time epoch.

In a preferred embodiment of the present invention the 3-point derivative and the maximum absolute value of the slope given by equation 7 below will be used to identify the earliest activation in the surface unipolar ECG signal, to identify the time epoch during the cardiac cycle that corresponds to the first indication of the site of the origin of the arrhythmia on the body surface $$\frac{dV(t_i)}{dt} = \frac{V(t_{i+1}) - V(t_{i-1})}{2*SI} \quad \text{(Eq. 7)}$$

where SI is the sampling interval.

The same model and algorithm used to identify the region of localized electrical activity in the organism are also used to identify the location of the tip of the catheter. An oscillatory low amplitude electrical signal is applied at the catheter tip, which permits the invention to discriminate between the catheter signal and the bio-electric signal. The signal from each electrode in the body is a sum of two components: the low frequency bio-electric signal and the high frequency catheter tip signal. The invention preferably utilizes a low-pass filter to select that component of the signal originating from bio-electric activity and a lock-in amplifier to select that component of the signal originating from the catheter tip signal.

The lock-in amplifier demodulates the signal from each electrode by the known catheter tip signal. This process has two consequences: (1) The effects of the bio-electric signal are removed, and (2) The signal from the catheter tip is altered so that it can be treated as a simple direct current (DC) dipole in the same manner as the bio-electric signal.

In order to detect the bio-electric signal of interest in preferred embodiments of the invention, the signal from each electrode is first low-pass filtered to remove the high-frequency signal due to the catheter tip. The low-pass filter cut-off frequency is adjusted so that it will remove that component of the signal due to the catheter tip signal, while leaving that component of the signal due to bio-electrical activity unaltered.

The catheter signal amplitude is chosen such that it is sufficiently low (e.g., less than 10 microamperes) that it will not induce unwanted bio-electric activity, yet high enough that it can be readily detected. The catheter signal frequency is sufficiently high that it lies far outside the bandwidth of the bio-electric signal of interest. At the same time, the catheter signal frequency is not so high that the frequency-dependent tissue impedance will differ significantly between the catheter frequency and the bio-electric signal frequency. A typical frequency is approximately 5 kHz. It should be understood that numerical values for the catheter signal amplitude and frequency are presented for illustrative purposes and are not intended to limit the scope of the invention.

Figure 3:
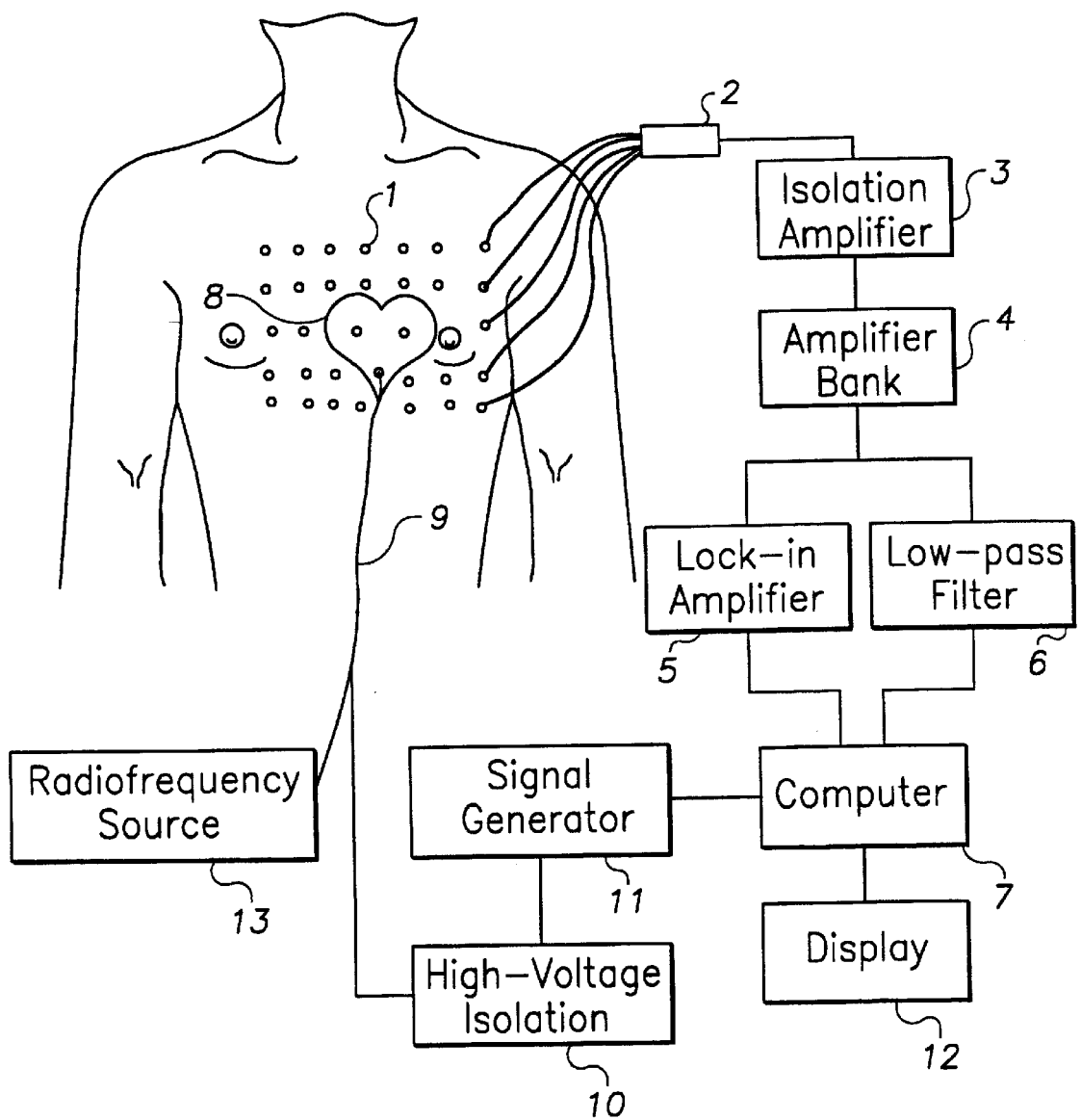
FIG. 3 is a schematic diagram of an apparatus for localizing a site of origin of an arrhythmia, guiding the delivery of ablative therapy, and delivering ablative therapy to the site of origin of the arrhythmia.

FIG. 3 shows a preferred embodiment of the apparatus for localizing an electrical source (e.g., the site of origin of an arrhythmia) within the heart, guiding the delivery of ablative energy, and delivering ablative energy to the vicinity of the electrical source. A multiplicity of passive electrodes are placed on the body surface of a subject (0) such that the heart may be viewed from the anterior, left lateral, right lateral, and posterior chest. Each electrode position is provided by the operator to analysis software included among the application programs of computer (7).

Signals from the passive electrodes (1) are carried in a multi-lead cable (2) through an isolation amplifier (3) to an amplifier bank (4) with adjustable gain and frequency response. A lock-in amplifier (5) is used to identify signals that are generated by the signal generator, emanate from the active electrode(s), and are acquired from the passive electrodes. A low-pass filter (6) is used to identify signals acquired from the passive electrodes that arise due to bio-electrical activity within the body. A computer (7) equipped with a multiplexor and an analog to digital conversion card digitizes and processes the signals emanating from a bio-electrical source within the body and the signals emanating from the active electrode. As described in detail above, in a preferred embodiment of the invention the processing step utilizes a single equivalent moving dipole (SEMD) model to localize both the bio-electrical source and the active electrode at a series of time epochs. In a preferred embodiment of the invention computer (7) includes application programs containing code (i.e., routines) for performing the algorithms and computations described above. The computer also creates an electronic representation of the signals acquired from each electrode, stores the signals, and displays the signals on a display (12). To inspect the signals the operator may display them off-line from storage at a rate slower than real time. The position, magnitude, and orientation of the SEMD attributed to cardiac electrical activity at each time epoch are displayed in a three-dimensional view of the heart. The uncertainty in the position of the SEMD and the goodness-of-fit value of the estimation of the SEND parameters may also be displayed for each time epoch.

The ablation catheter (9) with its at least one active electrode is placed in the heart (8) of the subject. The catheter is connected through a high-voltage isolation stage (10) that serves as an automatic switch (the switch automatically turns off the signal generator circuit after sensing the radiofrequency source) to a signal generator (11), which is controlled by the computer. The position, magnitude, and orientation of the dipole attributed to the tip of the catheter are displayed for each time epoch. The uncertainty in the position of the dipole attributed to the tip of the catheter and the goodness-of-fit value of the estimation of the dipole parameters attributed to the tip of the catheter are also displayed for each time epoch. A radio frequency source (13) controlled by the operator is also attached to the ablation catheter. After localization of the source of abnormal electrical activity (i.e., the site of origin of the arrhythmia) and positioning of the tip of the catheter at the source of abnormal electrical activity as described above, the catheter is used to deliver ablative radio frequency energy to the vicinity of the site of origin of the arrhythmia.

As discussed above, the location of the moving dipole, estimated by processing the electrical signals detected from the passive electrodes, is subject to distortion due to boundary effects and inhomogeneities in tissue conductivity. This distortion may in turn depend on the orientation (direction in 3-dimensional space) of the dipole. If the moving dipole generated by an active electrode located on the tip of the ablation catheter has a different orientation than the moving dipole generated by the electrical source, then when the estimated locations of the two moving dipoles are superposed by positioning of the active electrode, the actual locations of the two moving dipoles may still be offset. In one preferred embodiment, in order to reduce this offset a multiplicity of active electrodes are placed on the tip of the ablation catheter. Current is driven sequentially through different pairs of these active electrodes and resulting sets of potentials are detected on the passive electrodes. The different sets of potentials are then combined linearly and the location and moments of the moving dipole corresponding to the linear combination are computed. This procedure is continued (e.g., by computing the location and moments of the moving dipole corresponding to different linear combinations of the potentials) until the moving dipole associated with a particular linear combination of the different sets of potentials is approximately parallel to the moving dipole estimated for the electrical source.

In one preferred embodiment pulses are delivered through three different pairs of active electrodes respectively, resulting in sets of potential $\phi_1$, $\phi_2$, and $\phi_3$ respectively. Dipoles with moments $[P_{X1}, P_{Y1}, P_{Z1}]$, $[P_{X2}, P_{Y2}, P_{Z2}]$, $[P_{X3}, P_{Y3}, P_{Z3}]$ are estimated from the three respective sets of potentials measured on the passive electrodes. The values of these moments constitute a matrix M. If the moments of the estimated dipole corresponding to the electrical source are $[P_X', P_Y', P_Z']$ then a linear combination of the three sets of potentials $\Phi$ given by $$\Phi = M^{-1}\phi \qquad \text{(Eq. 8)}$$

where $M^{-1}$ is the inverse of the matrix M and $\phi$ is the column vector with elements $\phi_1$, $\phi_2$, and $\phi_3$, will provide an initial linear combination of the three sets of potentials from which a dipole approximately parallel to the dipole estimated for the electrical source is computed. Further adjustments in this combination may improve the degree of parallelness.

It is recognized that modifications and variations of the present invention will occur to those skilled in the art, and it is intended that all such modifications and variations be included within the scope of the appended claims.

What is claimed is:

1. A method for localizing an electrical source in the body comprising:

placing passive electrodes on the body;

placing at least one active electrode in the body;

acquiring from the passive electrodes signals emanating from the electrical source;

processing the signals emanating from the electrical source to determine the relative location of the electrical source;

delivering electrical energy to the at least one active electrode;

acquiring from the passive electrodes the signals emanating from the at least one active electrode;

processing the signals emanating from the at least one active electrode to determine the relative location of the at least one active electrode;

positioning the at least one active electrode to localize the electrical source.

2. A method for localizing an electrical source in the body comprising:

placing passive electrodes on the body;

placing at least one active electrode on the body;

acquiring from the passive electrodes signals emanating from the electrical source;

processing the signals emanating from the electrical source to determine the relative location of the electrical source;

delivering electrical energy to the at least one active electrode;

acquiring from the passive electrodes the signals emanating from the at least one active electrode;

processing the signals emanating from the at least one active electrode to determine the relative location of the at least one active electrode;

positioning the at least one active electrode to localize the electrical source.

3. A method for localizing an electrical source in the body comprising:

placing passive electrodes in the body;

placing at least one active electrode on the body;

acquiring from the passive electrodes signals emanating from the electrical source;

processing the signals emanating from the electrical source to determine the relative location of the electrical source;

delivering electrical energy to the at least one active electrode;

acquiring from the passive electrodes the signals emanating from the at least one active electrode;

processing the signals emanating from the at least one active electrode to determine the relative location of the at least one active electrode;

positioning the at least one active electrode to localize the electrical source.

4. A method for localizing an electrical source in the body comprising:
   placing passive electrodes in the body;
   placing at least one active electrode in the body;
   acquiring from the passive electrodes signals emanating from the electrical source;
   processing the signals emanating from the electrical source to determine the relative location of the electrical source;
   delivering electrical energy to the at least one active electrode;
   acquiring from the passive electrodes the signals emanating from the at least one active electrode;
   processing the signals emanating from the at least one active electrode to determine the relative location of the at least one active electrode;
   positioning the at least one active electrode to localize the electrical source.

5. The method of claim 1, 2, 3, or 4 wherein the positioning step involves approximating the relative locations of the at least one active electrode and the electrical source.

6. The method of claim 1, 2, 3, or 4 wherein the delivering step, the second acquiring step, the second processing step, and the positioning step are performed iteratively.

7. The method of claim 1, 2, 3, or 4 wherein the electrical source is located in the heart.

8. The method of claim 7 wherein the electrical source is the site of origin of an arrhythmia.

9. The method of claim 7 wherein the first processing step is used to determine the relative location of the electrical source at a multiplicity of time epochs during the cardiac cycle.

10. The method of claim 9 wherein the positioning step localizes the electrical source at one of the time epochs.

11. The method of claim 10 wherein at least one criterion is used to choose the time epoch.

12. The method of claim 1, 2, 3, or 4 wherein at least one of the processing steps comprises fitting the acquired signals to a moving dipole model.

13. The method of claim 1, 2, 3, or 4 wherein the first processing step further comprises fitting the signals emanating from the electrical source to a moving dipole, and the second processing step further comprises determining the relative location of a moving dipole that is approximately parallel to the moving dipole fitted in the first processing step.

14. The method of claim 13 wherein the at least one active electrode comprises a multiplicity of active electrodes.

15. A method for delivering ablative energy in the vicinity of the location of an electrical source comprising the method of claim 1, 2, 3, or 4 and further comprising the delivery of ablative energy in the vicinity of the location of the at least one active electrode.

16. The method of claim 15 wherein the ablative energy is radio frequency electrical energy.

17. The method of claim 15 wherein the at least one active electrode is located on a catheter.

18. The method of claim 17 wherein the ablative energy is delivered through the catheter.

19. The method of claim 1, 2, 3, or 4 wherein the electrical source is located in the brain.

20. The method of claim 3 or claim 4 wherein at least one of the passive electrodes is placed within the heart.

21. The method of claim 1, 2, 3, or 4 further comprising the displaying of the relative location of the electrical source.

22. The method of claim 1, 2, 3, or 4 further comprising the displaying of at least one measure selected from the group consisting of a measure of the size of an electrical source, a measure of the strength of an electric source, and a measure of the uncertainty in the relative location of the electric source.

23. A method for localizing an electrical source in the body comprising:
   placing passive electrodes on the body;
   placing at least one active electrode in the body;
   acquiring from the passive electrodes signals emanating from the electrical source;
   processing the signals emanating from the electrical source to determine the relative location of the electrical source at a multiplicity of time epochs during the cardiac cycle, wherein the processing involves fitting the signals to a moving dipole model;
   delivering electrical energy to the at least one active electrode;
   acquiring from the passive electrodes the signals emanating from the at least one active electrode;
   processing the signals emanating from the at least one active electrode to determine the relative location of the at least one active electrode, wherein the processing involves fitting the signals to a moving dipole model; and
   positioning the at least one active electrode to localize the electrical source at one of the time epochs, wherein at least one criterion is used to choose the time epoch; and wherein the delivering step, the second acquiring step, the second processing step, and the positioning step are performed iteratively.

24. A method for delivering ablative energy in the vicinity of the location of an electrical source comprising the method of claim 23 and further comprising the delivery of ablative energy in the vicinity of the location of the at least one active electrode, wherein the at least one active electrode is located on a catheter, wherein the ablative energy is delivered through the catheter, and wherein the electrical source is the site of origin of a cardiac arrhythmia.

25. An apparatus for localizing an electrical source within the body comprising:
   at least one passive electrode adapted for placement on the body;
   at least one active electrode adapted for placement in the body;
   a signal generator for delivering electrical energy to the at least one active electrode; and
   a computer for processing the signals emanating from the electrical source and the at least one active electrode to determine the relative location of the electrical source and the relative location of the at least one active electrode.

26. An apparatus for localizing an electrical source within the body comprising:
   at least one passive electrode adapted for placement on the body;
   at least one active electrode adapted for placement on the body;
   a signal generator for delivering electrical energy to the at least one active electrode; and
   a computer for processing the signals emanating from the electrical source and the at least one active electrode to determine the relative location of the electrical source and the relative location of the at least one active electrode.

27. An apparatus for localizing an electrical source within the body comprising:
- at least one passive electrode adapted for placement in the body;
- at least one active electrode adapted for placement on the body;
- a signal generator for delivering electrical energy to the at least one active electrode; and
- a computer for processing the signals emanating from the electrical source and the at least one active electrode to determine the relative location of the electrical source and the relative location of the at least one active electrode.

28. An apparatus for localizing an electrical source within the body comprising:
- at least one passive electrode adapted for placement in the body;
- at least one active electrode adapted for placement in the body;
- a signal generator for delivering electrical energy to the at least one active electrode; and
- a computer for processing the signals emanating from the electrical source and the at least one active electrode to determine the relative location of the electrical source and the relative location of the at least one active electrode.

29. The apparatus of claim 25, 26, 27, or 28 wherein the electrical source is located in the heart.

30. The apparatus of claim 29 wherein the electrical source is the site of origin of an arrhythmia.

31. The apparatus of claim 25, 26, 27, or 28 wherein the computer fits the signals emanating from the electrical source to a moving dipole model.

32. The apparatus of claim 25, 26, 27, or 28 wherein the computer fits the signals emanating from the at least one active electrode to a moving dipole model.

33. The apparatus of claim 25, 26, 27, or 28 wherein the computer fits the signals acquired from the passive electrodes to a moving dipole model.

34. An apparatus for delivering ablative energy in the vicinity of the location of an electrical source comprising the apparatus of claim 33 and further comprising:
- an isolation amplifier for isolating the signals acquired from the passive electrodes; and
- an amplifier bank for amplifying the signals acquired from the passive electrodes;
- a low-pass filter for identifying the signals originating from the electrical source;
- a lock-in amplifier for identifying the signals emanating from the at least one active electrode;
- a catheter, wherein the at least one active electrode is located on the catheter;
- a source of ablative energy for delivery in the vicinity of the at least one active electrode, wherein the ablative energy is delivered through the catheter; and
- a display.

35. The apparatus of claim 25, 26, 27, or 28 further comprising an isolation amplifier for isolating the signals acquired from the passive electrodes; and an amplifier bank for amplifying the signals acquired from the passive electrodes.

36. The apparatus of claim 25, 26, 27, or 28 further comprising a low-pass filter for identifying the signals emanating from the electrical source.

37. The apparatus of claim 25, 26, 27, or 28 further comprising a lock-in amplifier for identifying signals emanating from the at least one active electrode.

38. The apparatus of claim 25, 26, 27, or 28 further comprising a display.

39. An apparatus for delivering ablative energy in the vicinity of the location of an electrical source comprising the apparatus of claim 25, 26, 27, or 28 and further comprising a source of ablative energy for delivery in the vicinity of the at least one active electrode.

40. The apparatus of claim 39 further comprising a catheter.

41. The apparatus of claim 40 wherein the at least one active electrode is located on the catheter.

42. The apparatus of claim 41 wherein the ablative energy is delivered through the catheter.

43. The apparatus of claim 39 wherein the ablative energy is radio frequency electrical energy.

44. The apparatus of claim 25, 26, 27, or 28 wherein the electrical source is located in the brain.

* * * * *